US005366444A

United States Patent [19]
Martin

[11] Patent Number: 5,366,444
[45] Date of Patent: Nov. 22, 1994

[54] HAND OPERATED GUIDE WIRE ADVANCEMENT DEVICE

[75] Inventor: Geoffrey S. Martin, Mississauga, Canada

[73] Assignee: Med-Pro Design, Inc., Mississauga, Canada

[21] Appl. No.: 88,040

[22] Filed: Jul. 6, 1993

[51] Int. Cl.⁵ .............................................. A61M 5/178
[52] U.S. Cl. .................................... 604/159; 242/405; 242/615.3; 604/164; 128/772; 128/657
[58] Field of Search ...................... 604/159, 171, 164; 128/657, 772; 206/63.3; 242/96; 254/134.3

[56] References Cited

U.S. PATENT DOCUMENTS

| | | | |
|---|---|---|---|
| 4,858,810 | 8/1989 | Intlekofer et al. | 604/159 |
| 4,860,757 | 8/1989 | Lynch et al. | 128/657 |
| 4,917,094 | 4/1990 | Lynch et al. | 604/159 |
| 5,125,906 | 6/1992 | Fleck | 604/171 |

FOREIGN PATENT DOCUMENTS

| | | | |
|---|---|---|---|
| 207358 | 12/1967 | U.S.S.R. | |
| 092007606 | 5/1992 | WIPO | 604/159 |

Primary Examiner—John G. Weiss
Attorney, Agent, or Firm—Rogers & Scott

[57] ABSTRACT

A device is provided for feeding a guide wire into a hollow needle inserted into a patient's blood vessel to facilitate use of the wire for sliding a catheter over the wire into the blood vessel. The device includes an elongate coiled tube adapted to retain the wire with the wire in sliding engagement with the tube, and a discharge head coupled to one end of the tube. The head includes a guide opening adjacent the end of the tube, a platform having a surface adjacent the guide opening, and an outlet tip having a discharge opening. The platform is between the guide opening and the discharge opening the guide opening and discharge openings are proportioned to guide the wire in sliding contact with the wire and positioned to guide the wire over said surface. A depression in the platform faces the coiled tube and the depression is spaced from the end of the coiled tube sufficiently for the user to engage an index finger in the depression to stabilize the position of the device while the user pushes the wire along the surface on the platform using the thumb to thereby advance the wire out of the device.

12 Claims, 2 Drawing Sheets

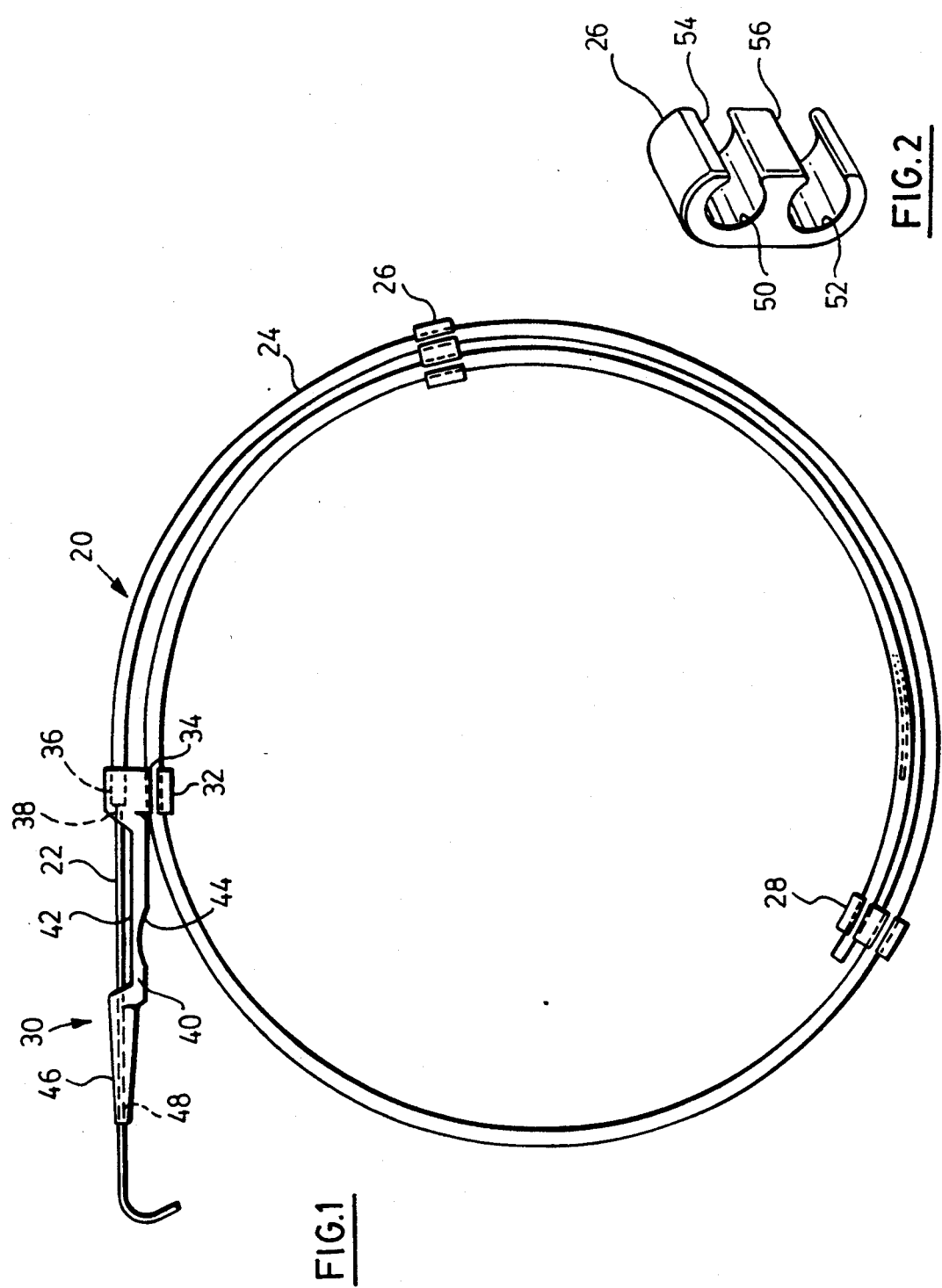

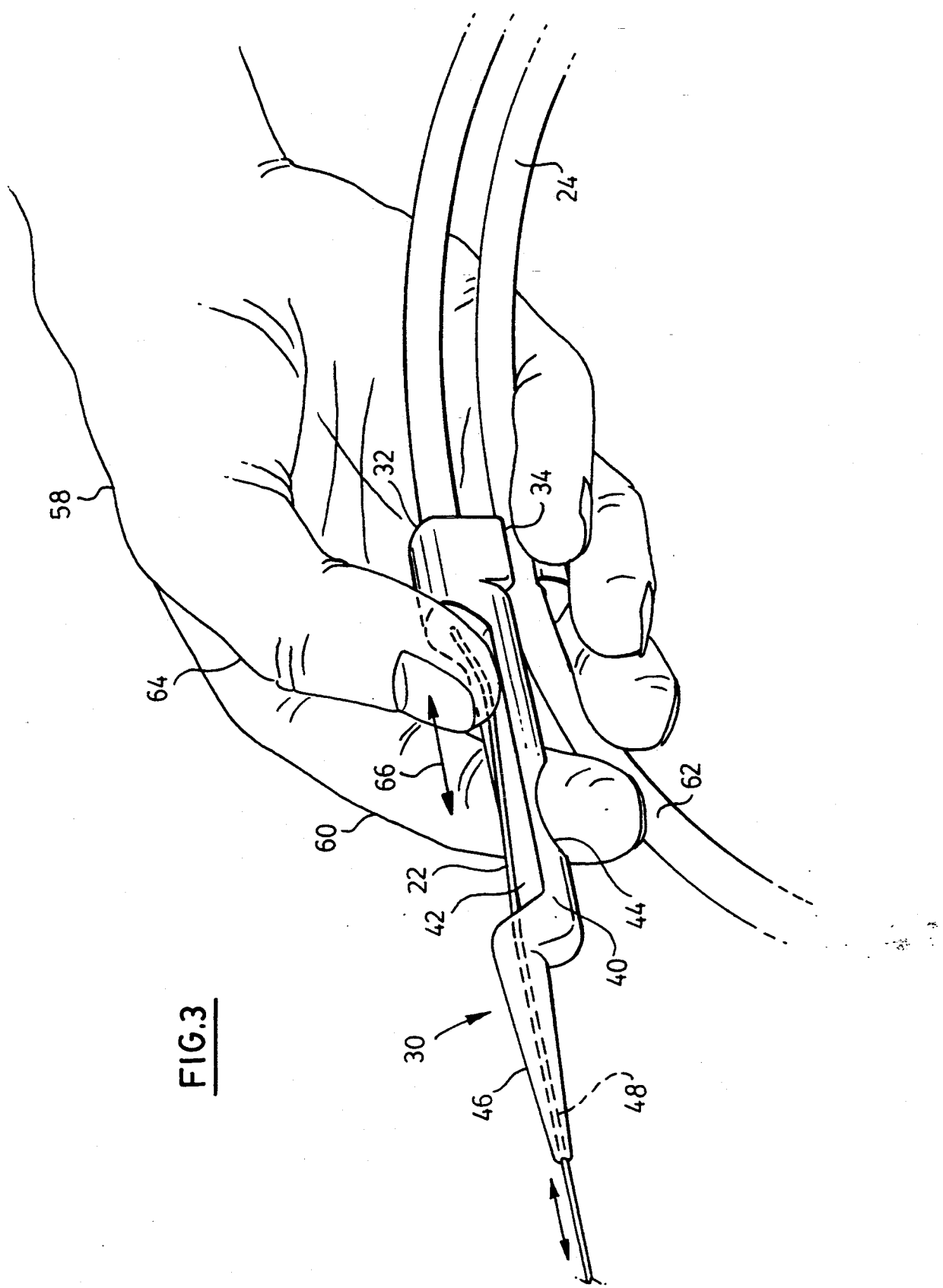

HAND OPERATED GUIDE WIRE ADVANCEMENT DEVICE

FIELD OF THE INVENTION

This invention relates to the insertion of catheter guide wires into blood vessels to facilitate catheter placement and in particular to a hand operated guide wire advancement device which can be operated using one hand.

BACKGROUND OF THE INVENTION

The Seldinger technique has become an accepted procedure for placing a catheter in a blood vessel. The technique involves first inserting a hollow needle into the blood vessel, advancing a guide wire through the hollow needle into the blood vessel, and then extracting the needle over the wire leaving the guide wire in place. A catheter can then be moved along the guide wire and into the blood vessel before the guide wire is removed.

Guide wires used for the above mentioned technique are usually made from stainless steel and include a tightly coiled spring wrapped around one or more axial core wires. Some guide wires have a very flexible pre-bent tip with a rounded leading end to facilitate insertion and to minimize the risk of damage to blood vessels as the wires are fed through these vessels. This type of guide wire (known as a "J" guide wire) is fed through a guide which is only slightly larger so that the pre-bent end is held straight as the wire is fed through the needle and into the blood vessel.

Guide wires, because of their length, are commonly packaged in a coiled tube dispenser to make handling less cumbersome. Also, the coil assists in keeping the wire in the sterile field. However insertion from the coil into a needle requires the use of one hand to hold the needle and an engagement piece guiding the wire into the needle while the other hand grips the wire between the coil and the engagement piece to move the wire forward from the coil into the needle.

It would be preferable to be able to advance the wire using one hand and this problem has been addressed in U.S. Pat. Nos. 4,860,757 and 5,125,906. These patents disclose devices in which a long guide wire is held in a flexible coiled tube having several turns so that the wire can be advanced from the Cube through a dispensing head and through the needle. The device must be gripped in a pinching action while the thumb is free to be used to advance the guide wire. These devices are somewhat awkward to hold and to use with one hand.

It is therefore an object of the invention to provide an improved hand operated guide wire advancement device which can be operated and easily controlled in one hand.

SUMMARY OF THE INVENTION

In one of its aspects the invention provides a device for feeding a guide wire into a hollow needle inserted into a patient's blood vessel to facilitate use of the wire for sliding a catheter over the wire into the blood vessel. The device includes an elongate coiled tube adapted to retain the wire with the wire in sliding engagement with the tube, and a discharge head coupled to one end of the tube. The head includes a guide opening adjacent the end of the tube, a platform having a surface adjacent the guide opening, and an outlet tip having a discharge opening. The platform is between the guide opening and the discharge opening and the guide and discharge openings are proportioned to guide the wire in sliding contact with the wire and positioned to guide the wire over said surface. A depression in the platform faces the coiled tube and the depression is positioned for the user to engage an index finger in the depression to stabilize the position of the device while the user pushes the wire along the surface on the platform using the thumb to thereby advance the wire out of the device.

In another of its aspects the invention provides a device for feeding a guide wire into a hollow needle inserted into a patient's blood vessel to facilitate use of the wire for sliding a catheter over the wire into the blood vessel. The device includes an elongate coiled tube adapted to retain the wire with the wire in sliding engagement with the tube, and a discharge head coupled to one end of the tube. The head includes a guide opening adjacent the end of the tube, a platform having a surface adjacent the guide opening, and an outlet tip having a discharge opening. The platform is between the guide opening and the discharge opening the guide opening and discharge openings are proportioned to guide the wire in sliding contact with the wire and positioned to guide the wire over said surface. A depression in the platform faces the coiled tube and the depression is spaced from the end of the coiled tube sufficiently for the user to resiliently engage an index finger in the space between the depression and the coiled tube to stabilize the position of the device while the user pushes the wire along the surface on the platform using the thumb to thereby advance the wire out of the device.

BRIEF DESCRIPTION OF THE DRAWINGS

FIG. 1 is a side view of a hand operated guide wire advancement device according to the invention and containing a guide wire;

FIG. 2 is a simplified isometric view of a clip used in the device (drawn to a larger scale than that used in FIG. 1) and which holds a tube of the device in a coiled condition; and FIG. 3 is a simplified isometric view showing the device in use and drawn to a larger scale than that used for FIG. 1.

DETAILED DESCRIPTION OF A PREFERRED EMBODIMENT OF THE INVENTION

Reference is made firstly to FIG. 1 which illustrates a device 20 for containing a guide wire 22 to permit a user to advance the guide wire out of the device and into a hollow needle (not shown) in preparation for a Seldinger introduction of a catheter over the wire. The device 20 includes a coiled tube 24 held in a coiled condition by a pair of tandem clips 26, 28 and by a discharge head indicated generally by the numeral As also seen in FIG. 1, the discharge head 30 includes a base 32 defining a side opening clip 34 receiving the tube 24, and a socket 36 which receives an end of the tube 24 and which terminates internally at a smaller guide opening 38 through which the wire 22 is free to slide. The base 32 is integrally attached to a platform 40 having an upper surface 42 adjacent the wire 22, and at its lower surface (as drawn) a curved depression 44 for purposes which will be explained. The platform ends at an outlet tip 46 which defines a discharge opening 48 proportioned to slidably receive the wire 22 in general alignment with the guide opening 38 in the base 32. The outlet tip 46 is tapered to engage in the proximal or outer end of a needle structure for location while the wire is pushed into the needle.

Reference is next made to FIG. 2 which illustrates tandem clip 26 which is exemplary also of clip 28. The clip 26 defines a pair of parallel recesses 50, 52 which are generally round in cross-section and have respective mouths 54, 56. The proportions are such that the mouths 54, 56 are smaller than the diameter of the tube 24 and the recesses 50, 52 are based on the same diameter as the tube 24. It is therefore possible to push the clip over the tube 24 into the position shown in FIG. 1. The arrangement is similar to that used for side opening clip 34 (FIG. 1) which has one recess to receive the tube.

Returning to FIG. 1, it will be seen that a significant length of wire can be contained in the device due to the fact that the tube is coiled and held in place by the tandem clips 26, 28 and by the clip 34 defined by the discharge head 30. The length of the tube, and the diameter of the coil can of course be varied and more or less clips used accordingly to retain the tube in a coiled condition.

The method of use of the device 20 will now be described with reference to FIG. 3 which illustrates a user's hand 58 holding the device with an index finger 60 located in the curved depression 44 and in engagement with a portion of the tube 62 adjacent the depression 44. The spacing between the curved depression 44 and the tube at portion 62 is such that the tube will be deflected slightly as the user enters an index finger and the tube will then tend to grip the user's index finger in position between the tube and the depression 44. This gripping action assists in maintaining the orientation of the device in relationship to the user's hand 58 leaving the thumb 64 free to move back and forwards as indicated by the arrow 66. The user will first pinch the wire in the position shown in FIG. 3, and then move thumb 64 to the left of FIG. 3 which will drive the wire through the device, and then, after releasing the wire, move the thumb back to start the cycle again. This will continue until the wire is in position whereupon the user can then disengage the index finger 60 and simply pull the device off the wire leaving the wire in position in the patient.

Returning to FIG. 1, it will be evident from the foregoing description of FIG. 3 that the distance between the curved depression 44 and the clip 34, and the curvature of the coil will determine the space for the index finger. In general, the space will be designed to be smaller than the average index finger and this will ensure that when the index finger is forced into position, the resiliency of the tube will be sufficient to hold the index finger in position. The resulting flexing of the tube will not be sufficent to interfere with the operation of the device.

It will be evident from the foregoing description that variations can be made within the scope of the invention. For instance, although the platform 40 has been shown to be straight, it could be curved and also, it is not essential that the outlet tip discharge opening 48 be in alignment with guide opening 38 provided of course that the wire travels freely between these openings. Also, the clip 34 could be made separately from the remainder of the discharge bead 30 although it will be appreciated that the portion of the clip is a critical part of design of the discharge head structure in order to maintain the relationship between the curved depression 44 and the tube 24.

It will also be evident that although all of the clips have been shown to be side opening, they could be formed differently and in fact it is not essential for all applications that the tube be disengaged from the clips. It would be possible for instance to close the clips so that the tube is threaded through the clips during assembly and left in place. It is also possible to use the device with the discharge head spaced from the coil. The user will then rely on the depression for location of the index finger. This is a natural action occurring as a nip between the index finger and the thumb.

These and other variations to the invention are within the scope of the disclosure and claims.

I claim:

1. A device for feeding a guide wire into a hollow needle inserted into a patient's blood vessel to facilitate use of the wire for sliding a catheter over the wire into the blood vessel, the device comprising:
   an elongate coiled tube adapted to retain the wire with the wire in sliding engagement within the tube;
   a discharge head coupled to one end of the tube, the head including a guide opening adjacent said end of the tube, a platform having a surface adjacent the guide opening, and an outlet tip having a discharge opening, the platform extending longitudinally between the guide opening and the discharge opening, and the guide opening and discharge being proportioned to be in sliding contact with the wire and positioned to guide the wire over said surface; and
   the platform defining a transverse depression positioned between the guide opening and the discharge opening and facing the coiled tube, the spacing between the platform and the coiled tube being selected such that the user can control the device by gripping the device in one hand with the index finger held in the depression by resilient engagement with the coiled tube, and the thumb being in contact with the wire to push the wire over said surface to thereby feed the guide wire.

2. A device as claimed in claim 1 in which the device further includes at least one tandem clip resiliently attached to the coiled tube to retain the tube in a coiled condition.

3. A device as claimed in claim 1 in which the guide opening and discharge opening are substantially in alignment one with the other and said surface is flat.

4. A device as claimed in claim 1 in which said depression is curved to match generally the roundness of an index finger.

5. A device as claimed in claim 1 in which said end of the tube is coupled to the discharge head by engagement in a socket formed in the discharge head.

6. In a guide wire device for moving a wire into a hollow needle and having a coiled tube for containing the wire and a discharge head providing for the user to advance the wire by pushing the wire longitudinally along a platform using the thumb, the improvement in which the platform defines a transversely depression facing the coiled tube and spaced from the coiled tube sufficient to combine with the tube resiliently receive the user's index finger so that the device can be gripped in one hand with the index finger in the depression and the thumb on the wire, the index finger and thumb combining to grip and advance the wire.

7. Structure as claimed in claim 6 in which the depression is curved to match generally the roundness of said index finger.

8. A device for feeding a guide wire into a hollow needle inserted into a patient's blood vessel to facilitate use of the wire for sliding a catheter over the wire into the blood vessel, the device comprising:

an elongate coiled tube adapted to retain the wire with the wire in sliding engagement within the tube;

a discharge head coupled to one end of the tube, the head including a guide opening adjacent said end of the tube, a platform having a surface extending longitudinally from the guide opening, and an outlet tip having a discharge opening, the platform being between the guide opening and the discharge opening, and the guide opening and discharge opening being proportioned to be in sliding contact with the wire and positioned to guide the wire over said surface; and the platform defining a transverse depression facing the coiled tube, the depression being spaced from said end of the coiled tube and the spacing between the depression and the coiled tube being selected such that the user is able to resiliently engage an index finger in the space between the depression and the coiled tube to stabilize the position of the device and the user's thumb is free to push the wire longitudinally along said surface to thereby advance the wire out of the device.

9. A device as claimed in claim 8 in which the device further includes at least one tandem clip resiliently attached to the coiled tube to retain the tube in a coiled condition.

10. A device as claimed in claim 8 in which the guide opening and discharge opening are substantially in alignment one with the other and said surface is flat.

11. A device as claimed in claim 8 in which said depression is curved to match generally the roundness of an index finger.

12. A device as claimed in claim 8 in which said end of the tube is coupled to the discharge head by engagement in a socket formed in the discharge head.

* * * * *